(12) United States Patent
Kojima

(10) Patent No.: US 10,488,370 B2
(45) Date of Patent: Nov. 26, 2019

(54) ULTRASOUND SENSOR WITH RESONANCE FREQUENCY ADJUSTMENT PORTION

(71) Applicant: Seiko Epson Corporation, Tokyo (JP)

(72) Inventor: Chikara Kojima, Matsumoto (JP)

(73) Assignee: Seiko Epson Corporation (JP)

( * ) Notice: Subject to any disclaimer, the term of this patent is extended or adjusted under 35 U.S.C. 154(b) by 117 days.

(21) Appl. No.: 15/323,662

(22) PCT Filed: Jul. 6, 2015

(86) PCT No.: PCT/JP2015/069455
§ 371 (c)(1),
(2) Date: Jan. 3, 2017

(87) PCT Pub. No.: WO2016/002971
PCT Pub. Date: Jan. 7, 2016

(65) Prior Publication Data
US 2017/0160242 A1    Jun. 8, 2017

(30) Foreign Application Priority Data

Jul. 4, 2014 (JP) .................................. 2014-139061

(51) Int. Cl.
*G01N 29/34* (2006.01)
*H01L 41/047* (2006.01)
(Continued)

(52) U.S. Cl.
CPC ............... *G01N 29/34* (2013.01); *A61B 8/04* (2013.01); *A61B 8/4444* (2013.01); *G01N 29/12* (2013.01);
(Continued)

(58) Field of Classification Search
CPC .................................................. H01L 41/253
(Continued)

(56) References Cited

U.S. PATENT DOCUMENTS 5,938,612 A * 8/1999 Kline-Schoder ........ B06B 1/064
310/334
7,427,797 B2 * 9/2008 Ohguro ................ B81B 3/0018
257/414
(Continued)

FOREIGN PATENT DOCUMENTS

JP        2005051685 A     2/2005
JP        2008-051656 A    3/2008
(Continued)

OTHER PUBLICATIONS

Merriam-Webster Dictionary, definition lateral (Year: 2014).*
(Continued)

*Primary Examiner* — Justin Seo
*Assistant Examiner* — David L Singer
(74) *Attorney, Agent, or Firm* — Harness, Dickey & Pierce, P.L.C.

(57) ABSTRACT

An ultrasound sensor includes a substrate having an opening portion, a diaphragm that blocks the opening portion, and an ultrasound element including a first electrode, a piezoelectric layer, and a second electrode that is laminated on the substrate. The first electrode, piezoelectric layer, and the second electrode are laminated onto the substrate on a side opposite of the opening portion of the diaphragm and overlap to form an active portion. A movable portion of the diaphragm is oscillatable by the active portion and a resonance frequency adjustment portion for adjusting a resonance frequency of the movable portion is provided on a lateral side of the active portion opposing the movable portion.

11 Claims, 9 Drawing Sheets

(51) Int. Cl.
| | |
|---|---|
| *H01L 41/08* | (2006.01) |
| *H01L 41/09* | (2006.01) |
| *H01L 41/113* | (2006.01) |
| *H04R 17/10* | (2006.01) |
| *G01N 29/12* | (2006.01) |
| *A61B 8/04* | (2006.01) |
| *A61B 8/00* | (2006.01) |
| *G01N 29/24* | (2006.01) |
| *B06B 1/06* | (2006.01) |
| *H01L 41/053* | (2006.01) |

(52) U.S. Cl.
CPC ......... *G01N 29/245* (2013.01); *H01L 41/047* (2013.01); *H01L 41/0825* (2013.01); *H01L 41/0973* (2013.01); *H01L 41/1132* (2013.01); *H04R 17/10* (2013.01); *A61B 8/4427* (2013.01); *A61B 8/4494* (2013.01); *B06B 1/0629* (2013.01); *G01N 29/2437* (2013.01); *G01N 2291/014* (2013.01); *H01L 41/053* (2013.01)

(58) Field of Classification Search
USPC .......................................................... 73/584
See application file for complete search history.

(56) References Cited

U.S. PATENT DOCUMENTS

| | | | | |
|---|---|---|---|---|
| 2002/0128556 A1* | 9/2002 | Nakamura | ............ | A61B 5/681 600/459 |
| 2002/0166218 A1* | 11/2002 | Barber | .............. | H04R 17/00 29/25.35 |
| 2007/0228880 A1* | 10/2007 | Higuchi | ................... | H03H 3/02 310/324 |
| 2008/0218560 A1* | 9/2008 | Noguchi | ............. | B41J 2/14233 347/71 |
| 2008/0231146 A1* | 9/2008 | Izumi | .................. | B41J 2/14233 310/358 |
| 2009/0301200 A1* | 12/2009 | Tanaka | ................. | B06B 1/0292 73/603 |
| 2009/0315645 A1* | 12/2009 | Watanabe | .......... | H03H 9/02409 333/186 |
| 2011/0007114 A1* | 1/2011 | Nakayama | ........... | B41J 2/14233 347/68 |
| 2011/0043575 A1* | 2/2011 | Nakayama | ........... | B41J 2/14233 347/68 |
| 2011/0291207 A1* | 12/2011 | Martin | .................. | G10K 9/125 257/416 |
| 2012/0056946 A1* | 3/2012 | Kojima | ................ | B41J 2/14233 347/70 |
| 2012/0099401 A1 | 4/2012 | Yamashita | | |
| 2012/0212546 A1* | 8/2012 | Yokoyama | ........... | B41J 2/14233 347/68 |
| 2012/0247217 A1* | 10/2012 | Suzuki | .................... | B25J 13/082 73/717 |
| 2013/0162102 A1* | 6/2013 | Sammoura | ........... | B06B 1/0292 310/321 |
| 2013/0245450 A1* | 9/2013 | Prins | ..................... | A61B 8/4494 600/459 |
| 2014/0018661 A1 | 1/2014 | Tsujita et al. | | |
| 2014/0103781 A1 | 4/2014 | Nakamura et al. | | |
| 2014/0111288 A1* | 4/2014 | Nikkel | ............... | H03H 9/02118 333/187 |
| 2014/0116147 A1 | 5/2014 | Endo | | |
| 2014/0118087 A1* | 5/2014 | Burak | .................... | H03H 9/173 333/186 |
| 2014/0118091 A1* | 5/2014 | Burak | .................... | H03H 9/132 333/187 |
| 2014/0152152 A1* | 6/2014 | Burak | ................ | H03H 9/02102 310/346 |
| 2014/0159548 A1* | 6/2014 | Burak | ................ | H03H 9/02118 310/346 |
| 2014/0225683 A1* | 8/2014 | Burak | .................... | H03H 9/173 333/187 |
| 2016/0329482 A1 | 11/2016 | Nakamura et al. | | |

FOREIGN PATENT DOCUMENTS

| | | |
|---|---|---|
| JP | 2010147658 A | 7/2010 |
| JP | 2010164331 A | 7/2010 |
| JP | 2010165028 A | 7/2010 |
| JP | 2010-210283 A | 9/2010 |
| JP | 2014-078906 A | 5/2014 |
| JP | 2014-086934 A | 5/2014 |
| WO | WO-2011001775 A1 | 1/2011 |
| WO | WO-2012124341 A1 | 9/2012 |

OTHER PUBLICATIONS

English Oxford Living Dictionaries, definition, lateral (Year: 2016).*
Webster's 1913 Dictionary, definition lateral, online edition (Year: 1913).*
Chen et al, High-power piezoelectric characteristics of manganese-modified BiScO3—PbTiO3 high-temperature piezoelectric ceramics, J. Phys. D: Appl. Phys. 45 (2012) 465303 (Year: 2012).*
Leontsev, Progress in engineering high strain lead-free piezoelectric ceramics, Sci. Technol. Adv. Mater. 11 (2010) 044302 (Year: 2010).*
Takenaka, Current Developments and Prospective of Lead-Free Piezoelectric Ceramics, Jpn. J. Appl. Phys., vol. 47, No. 5 (2008) (Year: 2008).*

* cited by examiner

A-A'

B-B'

ULTRASOUND SENSOR WITH RESONANCE FREQUENCY ADJUSTMENT PORTION

CROSS-REFERENCE TO RELATED APPLICATIONS

This application is a U.S. National Phase Application under 35 U.S.C. 371 of International Application No. PCT/JP2015/069455, filed on Jul. 6, 2015 and published in Japanese as WO 2016/002971 on Jan. 7, 2016. This application claims priority to Japanese Patent Application No. 2014-139061, filed on Jul. 4, 2014. The entire disclosures of the above applications are incorporated herein by reference.

TECHNICAL FIELD

The present invention relates to an ultrasound sensor.

BACKGROUND ART

Ultrasound sensors in which a semiconductor substrate having an opening portion, two layers of electrodes on an insulating film layer formed on the surface of the semiconductor substrate while blocking the opening portion and a PZT ceramic thin film layer interposed between the two layers of electrodes are arranged in an array form are known in the related art (for example, refer to JP-A-2010-164331).

In such an ultrasound sensor, a piezoelectric material forming the piezoelectric layer has to be replaced in order to control transmission sensitivity and reception sensitivity. That is, in a case where a dedicated transmission type element and a dedicated reception type element are provided, the elements having different piezoelectric materials have to be arranged, which is very difficult. In a case of unifying the piezoelectric materials, even though the transmission sensitivity and the reception sensitivity are able to be adjusted by varying, for example, a size of an opening portion, it is practically and actually difficult to use since a resonance frequency will be varied according to the varied size of the opening.

The invention was created in consideration of the above-described situation and an object thereof is to provide an ultrasound sensor in which the piezoelectric materials are the same and the elements having different transmission-reception sensitivity are provided together, without varying the resonance frequency.

SUMMARY

According to an aspect of the invention, there is provided an ultrasound sensor, including a substrate on which an opening portion is formed; a diaphragm which is provided on the substrate so as to block the opening portion; and ultrasound elements which include a first electrode, a piezoelectric layer and a second electrode and which are laminated on an opposite side to the opening portion of the diaphragm, in which, when a direction in which the first electrode, the piezoelectric layer and the second electrode are laminated is referred to as a Z-direction, a portion in which the first electrode, the piezoelectric layer and the second electrode are overlapped in the Z-direction is referred to as an active portion, and a portion which is a range to the extent that the diaphragm is oscillatable by driving the active portion is referred to as a movable portion, the active portion is arranged opposite to the movable portion; the active portion has a smaller profile than that of the movable portion in plan view; and a resonance frequency adjustment portion for adjusting a resonance frequency is provided on a lateral side of the active portion, at least in a region opposite to the movable portion.

In the aspect, even if, for example, the resonance frequency of the ultrasound elements which are optimized to the dedicated transmission type or the dedicated reception type varies, the ultrasound elements which share the same resonance frequency and are optimized to the dedicated transmission type and the dedicated reception type can be provided, transmission and reception can be efficiently performed, and the reliability can be improved by providing the resonance frequency adjustment portion and adjusting the resonance frequency.

It is preferable that, in plan view, the active portion is in a rectangle shape, and the resonance frequency adjustment portion is provided on a lateral side of a long side of the rectangle shape. Thereby, the resonance frequency can be adjusted more efficiently by the resonance frequency adjustment portion, and the ultrasound elements which are optimized to the dedicated transmission type and the dedicated reception type can be provided.

It is preferable that, when two directions which are orthogonal to each other and also orthogonal to the Z-direction are referred to as an X-direction and a Y-direction, a plurality of the movable portions and the active portions are arranged in the X-direction and/or Y-direction. Thereby, the transmission and reception can be efficiently performed along the X-direction and the Y-direction.

It is preferable that the resonance frequency adjustment portions are provided on lateral sides of a portion of the plurality of the active portions, while the resonance frequency adjustment portions are not provided on lateral sides of other portion of the plurality of the active portions. Thereby, the ultrasound elements which share the same resonance frequency and are optimized to the dedicated transmission type and the dedicated reception type can be established more reliably by providing the resonance frequency adjustment portion on the ultrasound elements having different resonance frequency.

It is preferable that two or more types of the active portions are provided, each of which has the piezoelectric layer having a different width such that the width is a length of any one of the sides in the X-direction or the Y-direction in a case where the active portion is in a square shape and the width is a length of a short side in a case where the active portion is in a rectangle shape, in plan view. Thereby, the ultrasound elements which share the same resonance frequency by the resonance frequency adjustment portion and are optimized to the dedicated transmission type and the dedicated reception type can be established by adjusting the width of the piezoelectric layer.

It is preferable that two or more types of the active portions are provided, each of which has the piezoelectric layer having a different thickness. Thereby, the ultrasound elements which share the same resonance frequency by the resonance frequency adjustment portion and are optimized to the dedicated transmission type and the dedicated reception type can be established by adjusting the width of the piezoelectric layer.

It is preferable that the plurality of ultrasound elements include the ultrasound element set as a dedicated reception type and the ultrasound element set as a dedicated transmission type. Thereby, the ultrasound elements which are optimized to the dedicated transmission type and the dedicated reception type can be provided without changing the piezoelectric material.

It is preferable that the resonance frequency adjustment portion is composed of a material different from those of the first electrode, the piezoelectric layer and the second electrode. Thereby, the resonance frequency adjustment portion can be provided by providing films formed by different materials.

It is preferable that the resonance frequency adjustment portion is a bonding portion which is provided on a bonding substrate bonded to a side on which the ultrasound elements of the substrate are provided. Thereby, the resonance frequency adjustment portion can be provided by bonding the bonding substrate.

DETAILED DESCRIPTION

Figure 1:
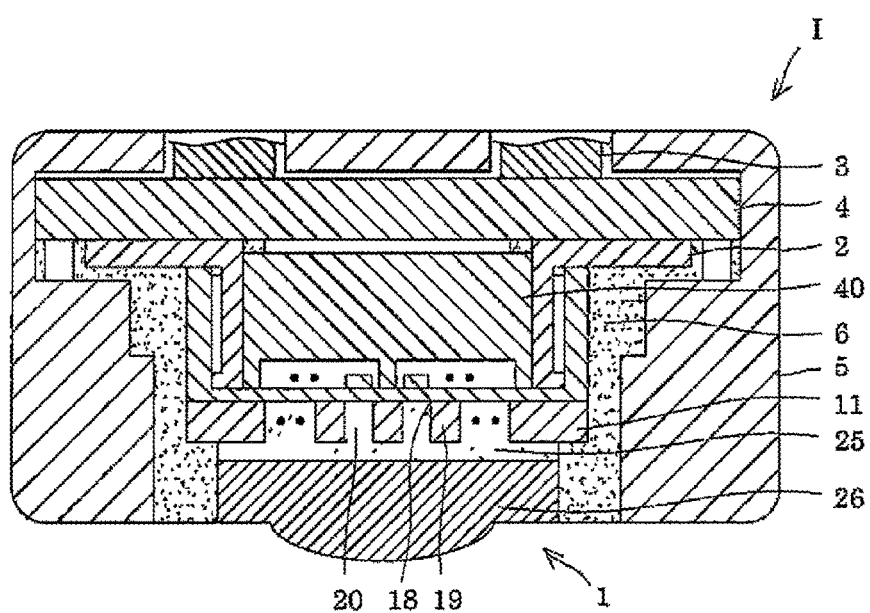
FIG. 1 is a cross-sectional view illustrating a configuration example of an ultrasound device according to Embodiment 1.

Below, embodiments of the invention will be described with reference to the drawings. The description below illustrates one form of the invention, and arbitrary modifications are possible within the scope of the invention. In the respective drawings, portions given the same reference numeral illustrate the same members, and description thereof will not be made, as appropriate.

Embodiment 1 Ultrasound Device FIG. 1 is a cross-sectional view illustrating a configuration example of an ultrasound device on which the ultrasound sensor according to Embodiment 1 of the invention is mounted. As illustrated in FIG. 1, the ultrasound probe I is formed including a CAV surface type ultrasound sensor 1, a flexible printed substrate (FPC substrate 2) connected to the ultrasound sensor 1, a cable 3 drawn out from an apparatus terminal (not shown), a relay substrate 4 that serves as an intermediate between the FPC substrate 2 and the cable 3, a housing 5 that protects the ultrasound sensor 1, the FPC substrate 2 and the relay substrate 4, and a waterproof resin 6 which fills the space between the housing 5 and the ultrasound sensor 1.

Ultrasound waves are transmitted from the ultrasound sensor 1. Ultrasound waves reflected from a measurement target are received by the ultrasound sensor 1. Information (such as position and shape) pertaining to the measurement target is detected in the apparatus terminal of the ultrasound probe I based on the waveform signal of the ultrasound waves.

According to the ultrasound sensor 1, it is possible to ensure high reliability, as described later. Accordingly, by mounting the ultrasound sensor 1, an ultrasound device with various superior characteristics is formed. It is possible to also apply the invention to any ultrasound sensor 1, such as a dedicated transmission type optimized to the transmission of ultrasound waves, a dedicated reception type optimized to the reception of ultrasound waves, and a transmission and reception integrated type optimized to the transmission and reception of ultrasound waves. The ultrasound device on which the ultrasound sensor 1 is able to be mounted is not limited to the ultrasound probe I.

Figure 2:
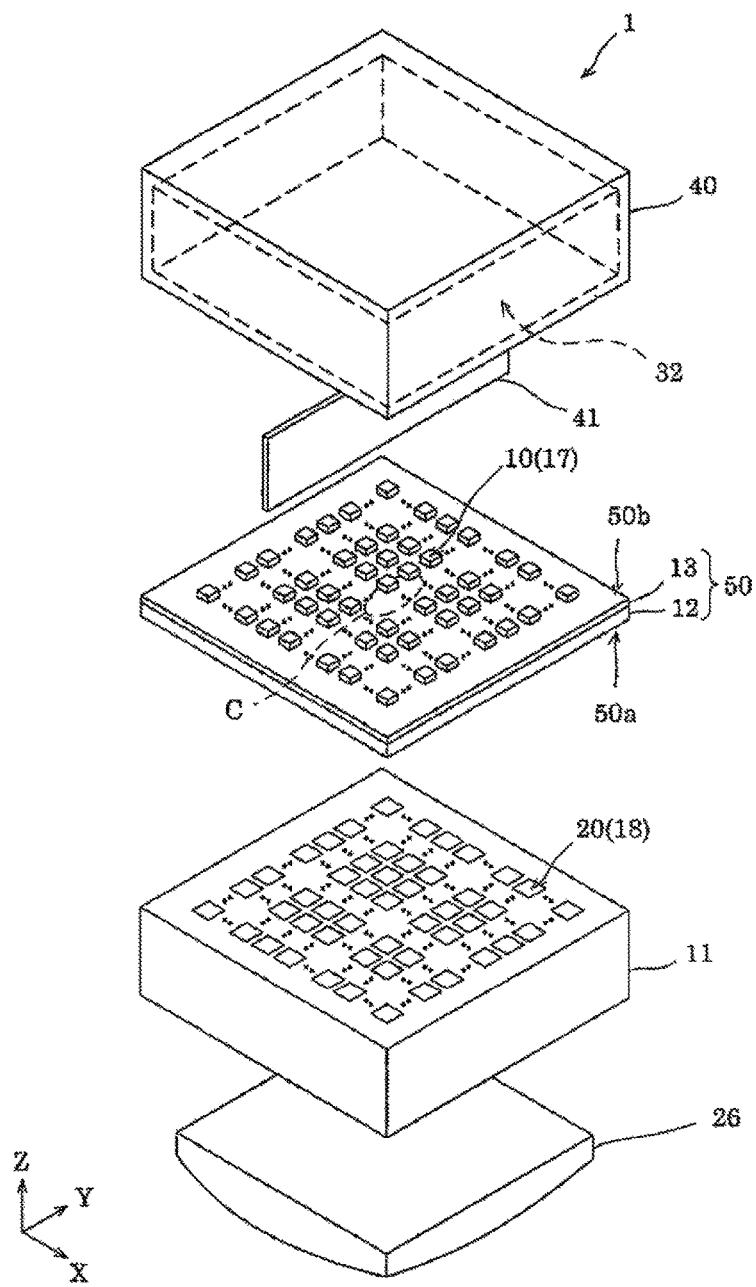
FIG. 2 is an exploded perspective view illustrating a configuration example of an ultrasound sensor according to Embodiment 1.
Figure 3:
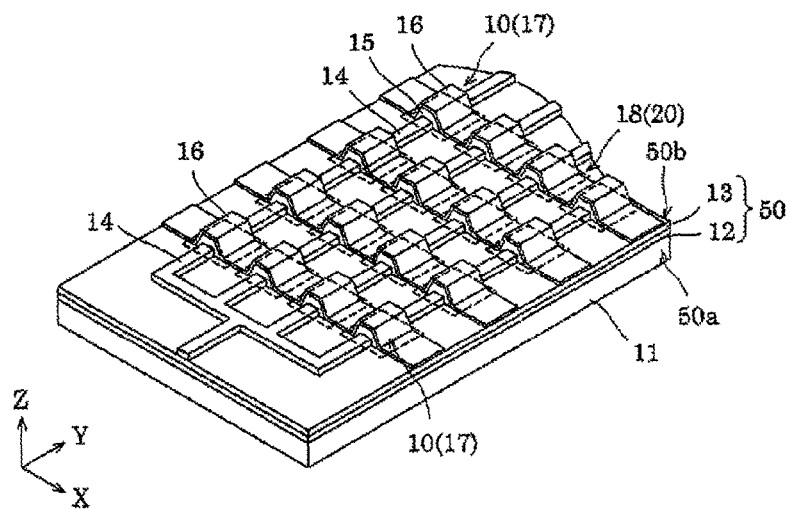
FIG. 3 is an enlarged perspective view illustrating a configuration example of an ultrasound element array.
Figure 4:
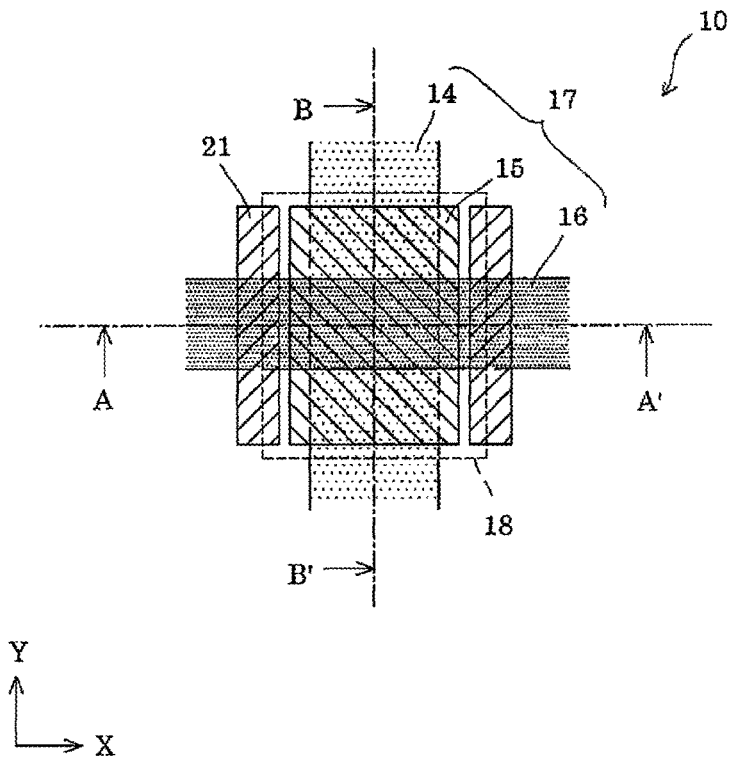
FIG. 4 is a plan view illustrating a schematic configuration of the ultrasound element according to Embodiment 1.
Figure 5A:
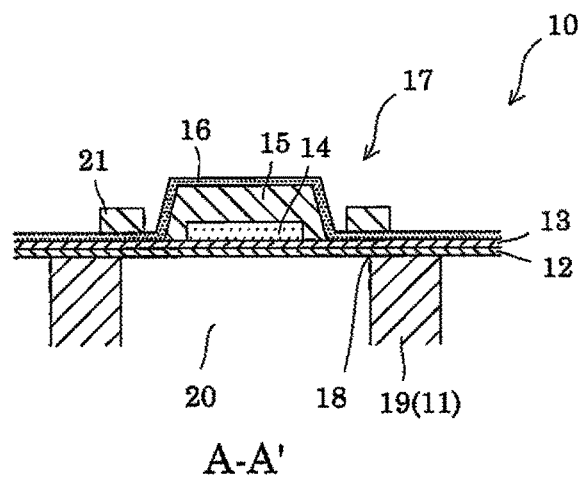
FIG. 5A and FIG. 5B show cross-sections of the ultrasound element according to Embodiment 1.
Figure 5B:
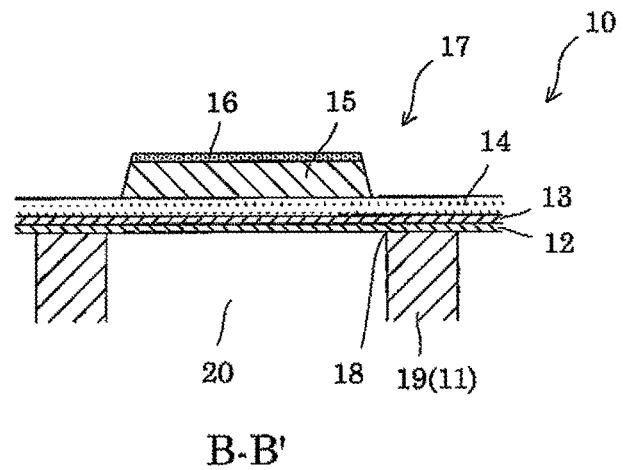
Figure 6:
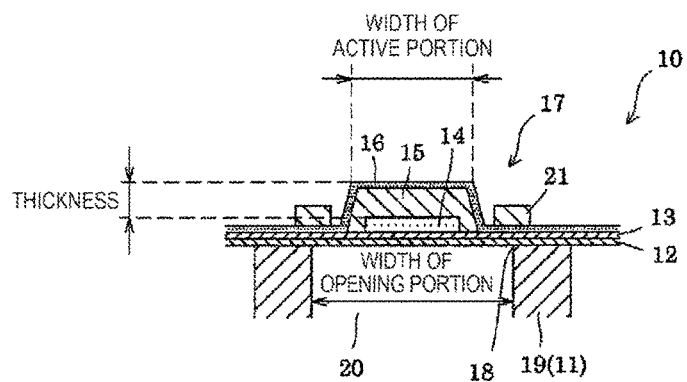
FIG. 6 is a schematic diagram of the ultrasound element according to Embodiment 1.

Ultrasound Sensor FIG. 2 is an exploded perspective view of the ultrasound sensor. FIG. 3 is an enlarged perspective view illustrating a configuration example of an ultrasound sensor element array. FIG. 4 is a plan view illustrating a schematic configuration of the ultrasound element according to Embodiment 1 of the invention, FIG. 5A is a cross-sectional view taken along line A-A' and FIG. 5B is a cross-sectional view taken along line B-B', and FIG. 6 is a schematic diagram of the ultrasound element.

The ultrasound sensor 1 is formed including an ultrasound element 10, an acoustic matching layer 25, a lens member 26, and an enclosure plate 40. The ultrasound element 10 is formed including a substrate 11, a diaphragm 50, and a piezoelectric element 17. In FIG. 2, although the enclosure plate 40 and a support member 41 are depicted as separate bodies, in practice, both are integrally formed.

When two mutually orthogonal axes are the X-axis and the Y-axis and the plane formed by the X-axis and the Y-axis is the XY-plane, the substrate 11 follows the XY-plane. Below, the X-axis is referred to as the first direction X, the Y-axis as the second direction Y, and the Z-axis direction which is orthogonal to both of the first direction X and the second direction Y as the third direction Z.

A plurality of dividing walls 19 are formed on the substrate 11. A plurality of spaces 20 are divided along the first direction X and the second direction Y by the plurality of dividing walls 19. The spaces 20 are formed so as to pass through the substrate 11 in the third direction Z. The spaces 20 are formed in a two-dimensional form, that is, a plurality in the first direction X and a plurality in the second direction Y. The arrangement or shape of the spaces 20 can be modified in various ways. For example, the spaces 20 may also be formed in a one-dimensional form, that is, along one direction of either of the first direction X and the second direction Y. The spaces 20 may also have a long shape (a ratio of lengths in the first direction X and the second direction Y other than 1:1) when viewed from the third direction Z.

The diaphragm 50 is provided on the substrate 11 so as to block an opening portion 18 formed of the space 20. Below, the surface on the substrate 11 side of the diaphragm 50 is referred to as a first surface 50a, and the surface facing the first surface 50a is referred to as a second surface 50b. The diaphragm 50 is formed of an elastic film 12 formed on the substrate 11 and an insulator film 13 formed on the elastic film 12. In this case, the first surface 50a is formed of the elastic film 12 and the second surface 50b of the insulator film 13.

Hereinafter, the ultrasound element will be described in detail.

As illustrated in FIG. 4, the ultrasound element 10 of the embodiment is formed of the elastic film 12 formed of a silicon dioxide film provided on one surface of the substrate 11 formed of a silicon substrate and the piezoelectric element 17 which is formed on the insulator film 13 formed of zirconium oxide and which formed of a first electrode 14, a piezoelectric layer 15, and a second electrode 16. The opening portion 18 is formed in a region corresponding to the piezoelectric element 17 of the substrate 11, and the space 20 forming the opening portion 18 is divided by the dividing wall 19.

Although it is possible to use a single-crystal silicon substrate as the substrate 11, there is no limitation thereto. In the embodiment, although the diaphragm 50 is configured by the elastic film 12 formed of silicon dioxide or the like and the insulator film 13 formed of zirconium oxide or the like, there is no limitation thereto, and either one may be used or another film may be used.

The piezoelectric element 17, which is formed of the first electrode 14, the piezoelectric layer 15 with a thin film thickness of 3 μm or less and preferably 0.3 μm to 1.5 μm, and a second electrode 16 with an adhesive layer interposed as necessary, is formed on the insulator film 13. Here, the piezoelectric element 17 refers to the portion that contains the first electrode 14, the piezoelectric layer 15, and the second electrode 16. A region interposed between the first electrode 14 and the second electrode 16 is referred to an active portion.

In general, in a case of driving the piezoelectric element 17, although either one of the electrodes is a common electrode and the other electrode is an individual electrode, in the ultrasound element 10, since driving and scanning are performed for each plurality of ultrasound elements 10, it is not realistic to distinguish which one is the common electrode and which is the individual electrode. In any case, in a case of using a form in which the ultrasound elements 10 are arranged one-dimensionally or two-dimensionally, it is possible to drive only a predetermined piezoelectric element 17 by providing the first electrode 14 so as to span in one direction, provide the second electrode 16 so as to span in a direction orthogonal to the one direction, and applying a voltage between the first electrode 14 and the second electrode 16 selected, as appropriate. When selecting the predetermined piezoelectric element 17, the driving is generally performed by selecting one row or a plurality of rows as one group. In the embodiment, four rows of the first electrodes 14 are bound and shared. This is tentatively referred to as 1-channel, and a plurality of channels are provided spanning the first direction X. The second electrode 16 is continuously provided as one row along the first direction X, and a plurality of rows is provided along the second direction Y.

In such a configuration, when all rows of the second electrodes 16 are shared, all of the piezoelectric elements 17 in the 1-channel are driven at the same time and each channel is driven sequentially, it is possible to acquire data of one dimension along the first direction X.

When the second electrodes 16 are shared one row at a time or a plurality of rows at a time, the piezoelectric elements 17 in 1-channel are shared by the second electrodes 16 and sequentially driven a group at a time, and each channel is sequentially driven, it is possible to acquire two-dimensional data in the XY direction.

Hereafter, the combination of the piezoelectric element 17, and the elastic film 12 and the insulator film 13 which are the diaphragm 50 in which displacement occurs due to driving of the piezoelectric element 17 are referred to as an actuator apparatus. In the above-described examples, although the elastic film 12 and the insulator film 13, the adhesive layer which is provided as necessary, and the first electrode 14 act as the diaphragm 50, there is no limitation thereto. For example, the diaphragm 50 need not be provided, and the piezoelectric element 17 itself may substantially serve as the diaphragm.

In the piezoelectric element 17, the active portion indicates a portion in which the first electrode 14, the piezoelectric layer 15 and the second electrode 16 are overlapped in plan view and also a region in which the piezoelectric layer 15 is interposed between the first electrode 14 and the second electrode 16. Furthermore, the movable portion refers to a region in which the first electrode 14 and the second electrode 16, in addition to the elastic film 12 and the insulator film 13, also serve as the diaphragm 50 blocking the opening portion 18 and which corresponds to the opening portion 18 of the diaphragm 50, i.e. a region in which the diaphragm 50 can be oscillated by driving the piezoelectric element 17. The active portion corresponds to the movable portion one-to-one. In Embodiment 1 of the invention, the active portion corresponds to the opening portion 18 one-to-one. However, one opening portion 18 may contain a plurality of the active portions in plan view. In this case, the active portion can substantially correspond to the movable portion one-to-one by providing, for example, a columnar partition, which suppresses the oscillation of the diaphragm 50, between the neighboring active portions and limiting a region in which the diaphragm 50 can be oscillated within the opening portion 18.

The first electrode 14 and the second electrode 16 are not limited as long as they have conductivity and it is possible to use metal materials, such as platinum (Pt), iridium (Ir), gold (Au), aluminum (Al), copper (Cu), titanium (Ti), and stainless steel; tin oxide-based conductive materials, such as indium tin-oxide (ITO), and fluorine-doped tin oxide (FTC); zinc-oxide-based conductive materials, conductive oxides, such as strontium ruthenate ($SrRuO_3$), lanthanum nickelate ($LaNiO_3$), element doped strontium titanate; and conductive polymers. However, there is no restriction to these materials.

It is possible to use a complex oxide with a lead zirconate titanate (PZT)-based perovskite structure for the piezoelectric layer 15, as a representative. Thereby, the displacement amount of the piezoelectric element 17 is easily ensured.

The piezoelectric layer 15 does not include lead, and, for example, it is possible to use a complex oxide with a perovskite structure which includes at least bismuth (Bi), barium (Ba), iron (Fe), and titanium (Ti). Thereby, it is possible to realize the ultrasound element 10 using a non-lead based material with a low load on the environment.

The A site of such a perovskite structure, that is, an ABO3 type structure, is coordinated with 12 oxygen atoms, and, in addition, the B site is coordinated with 6 oxygen atoms, thereby forming an octahedron. In the example of the above-described piezoelectric layer 15 which does not contain lead, the Bi, Ba, and Li are positioned at the A site and the Fe and Ti are positioned at the B site.

In the complex oxide which includes a perovskite structure including Bi, Ba, Fe, and Ti, although the constitution formula is represented by (Bi, Ba) (Fe, Ti)$O_3$, a representative constitution is represented as a mixed crystal of bismuth ferrate and barium titanate. The bismuth ferrite and barium titanate of the mixed crystal are not detected singly in an X-ray diffraction pattern. Constitutions deviating from the constitution of the mixed crystal are also included.

Constitutions shifted from the stoichiometric constitution due to lack or excess or in which a portion of the elements are substituted with other elements are also included in the complex oxide with a perovskite structure. That is, as long as a perovskite structure is obtainable, the inevitable deviations in the constitution due to lattice mismatching, oxygen faults and the like such as partial substitution of elements are naturally also permissible.

The configuration of the complex oxide with a perovskite structure is not limited to the examples, and the configuration may include other elements. It is preferable that the piezoelectric layer 15 further include manganese (Mn). Thereby, leakage current is suppressed and it is possible to realize a high-reliability ultrasound element 10 as a non-lead based material.

Bi at the A site of the piezoelectric layer 15 may be substituted with lithium (Li), samarium (Sm), cerium (Ce) or the like, and the Fe at the B site may be substituted with aluminum (Al), cobalt (Co), and the like. Thereby, various characteristics are improved, thereby easily achieving diversification of the configuration and function. Even in the case of a compound oxide including these other elements, it is preferable that the configuration have a perovskite structure.

In Embodiment 1 of the invention, the movable portion refers to a region in which the first electrode 14 and the second electrode 16, in addition to the elastic film 12 and the insulator film 13, also serve as the diaphragm 50 blocking the opening portion 18 and which corresponds to the opening portion 18 of the diaphragm 50, i.e. a region in which the diaphragm 50 can be oscillated by driving the piezoelectric element 17, as described above.

Furthermore, in Embodiment 1 of the invention, the active portion is in a rectangle shape which has the second direction Y as the longitudinal direction and the first direction X as the transverse direction, i.e. a rectangle shape in which a side along the second direction Y is a long side (longitudinal plane) and a side along the first direction X is a short side (transverse plane), in a plan view. A relationship between a length in the transverse direction, that is, a length of the short side of the active portion and a length in the direction X of the opening portion 18 has a big influence on the resonance frequency.

In Embodiment 1 of the invention, resonance frequency adjustment films 21 are provided on lateral sides of the long sides at both sides in a width direction, i.e. the transverse direction of the active portion, separating from the active portion, as a resonance frequency adjustment portion. The resonance frequency adjustment film 21 is provided so as to straddle from a region opposite to the opening portion 18 of the diaphragm 50 on a lateral side of the long side of the active portion to a region opposite to the dividing wall 19. Such resonance frequency adjustment film 21 adjusts the resonance frequency by serving as a weight of the diaphragm 50 which is provided on the lateral side of the long side of the active portion and oscillates mostly, as described above. In a case where the active portion is in a square shape in plan view, the width direction may be any direction and the resonance frequency adjustment film 21 may be provided on a lateral side of any side.

The material of the resonance frequency adjustment film 21 is not particularly limited. It may be formed of, for example, a conductive material the same as that of a lead wiring, such as gold or copper, or an insulating material such as alumina or zirconia.

Figure 7:
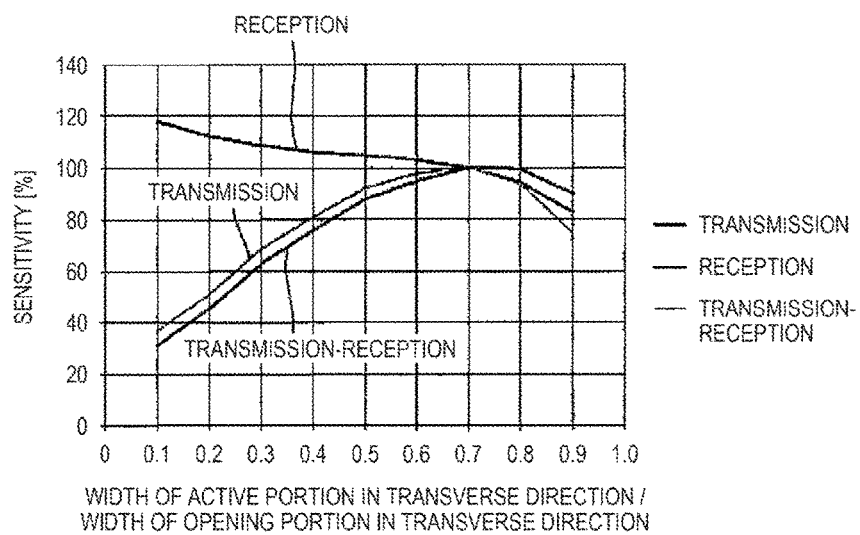
FIG. 7 is a relationship diagram between width of the active portion in transverse direction/width of the opening portion in transverse direction and transmission-reception sensitivity.
Figure 8:
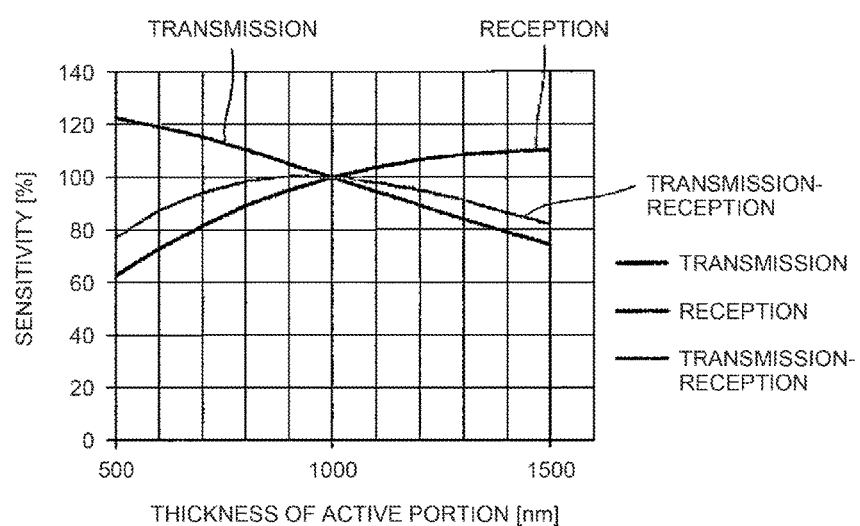
FIG. 8 is a relationship diagram between thickness of the active portion and the transmission-reception sensitivity.

FIG. 6 shows a cross-section of the ultrasound element 10 in the transverse direction, and indicates the width and the thickness of the active portion. In such ultrasound element 10, the width and the thickness of the active portion have a big influence on the transmission-reception sensitivity. FIG. 7 shows a relationship between the width of the active portion in the transverse direction/the width of the opening portion in transverse direction and transmission-reception sensitivity. FIG. 8 shows a relationship between the thickness of the active portion and the transmission-reception sensitivity.

As illustrated in such drawings, the reception sensitivity increases but the transmission sensitivity decreases as the width of the active portion in the transverse direction/the width of the opening portion in transverse direction becomes smaller. The transmission sensitivity increases but the reception sensitivity decreases as the thickness of the active portion becomes smaller, while the reception sensitivity increases but the transmission sensitivity decreases as the thickness of the active portion becomes larger.

The transmission sensitivity is proportional to an excluded volume v due to the displacement of the movable portion based on driving of the active portion. The excluded volume v is proportional to a dimension S of the active portion. Moreover, the excluded volume v is proportional to a degree of distortion δ of the piezoelectric element. The distortion δ is proportional to a value of $d31 \times Vh/t$ (d31 indicates a piezoelectric constant, Vh indicates an applied voltage, and t indicates a thickness of the piezoelectric element (active portion)). Thus, the excluded volume v is inversely proportional to the thickness of the piezoelectric element.

The results shown in FIGS. 7 and 8 are consistent with this theory.

In Embodiment 1 of the invention, the reception sensitivity is evaluated based on voltage generated by the reception. The generated voltage V is represented by $V=Q/C$ (Q indicates generated charge and C indicates a capacitance) and is inversely proportional to the capacitance of the piezoelectric element. The capacitance C is represented by $\epsilon 0 \times \epsilon r \times (S/t)$ (ε0 indicates a vacuum permittivity, εr indicates a relative permittivity of the piezoelectric element, S indicates the dimension of the active portion and t indicates a thickness of the piezoelectric element (active portion)). The smaller the dimension S is, the smaller the capacitance C is. The larger the thickness t is, the smaller the capacitance C is. That is, the reception sensitivity increases as the dimension becomes smaller or the thickness becomes larger in the active portion. The results shown in FIGS. 7 and 8 are consistent with this theory.

In a case where the reception sensitivity is evaluated based on the generated charge Q, the results are different from those described above. However, the piezoelectric constant g31, pressure of a sound wave to be received or the dimension of the active portion has to be increased in order to increase the generated charge Q, each of which is too difficult to realize. Thus, it is very efficient that the capacitance C is decreased by adjusting the dimension or thickness of the active portion while the reception is evaluated based on the generated voltage as described above.

Therefore, it is possible to use the ultrasound element 10 which is optimized to the dedicated transmission type and has improved transmission sensitivity and the ultrasound element 10 which is optimized to the dedicated reception type and has improved reception sensitivity at the same time, each of which enhances the sensitivity by properly adjusting the dimension of the opening portion, the width of the active portion in the transverse direction, and the thickness of the active portion. However, the resonance frequency is also changed when varying the width of the active portion in the transverse direction/the width of the opening portion in transverse direction or the thickness of the active portion.

In the ultrasound sensor 1 of Embodiment 1 of the invention, the ultrasound element 10 which is optimized to the dedicated transmission type and has improved transmission sensitivity and the ultrasound element 10 which is optimized to the dedicated reception type and has improved reception sensitivity can be used at the same time, each of which enhances the sensitivity by properly adjusting the dimension of the opening portion, the width of the active portion in the transverse direction, and the thickness of the active portion. Furthermore, the ultrasound element 10 optimized to the dedicated reception type and the ultrasound element 10 optimized to the dedicated transmission type share the substantially same resonance frequency by adjusting the resonance frequency with the resonance frequency adjustment film 21.

With such a configuration, it is possible to significantly improve the transmission sensitivity and the reception sensitivity at the same time by providing the ultrasound element 10 optimized to the dedicated reception type and the ultrasound element 10 optimized to the dedicated transmission type together in a state where they share the uniform resonance frequency.

In general, the ultrasound elements 10 of the ultrasound sensor 1 are arranged two-dimensionally in the first direction X and the second direction Y orthogonal thereto, and the first direction X and the second direction Y are the scanning direction and the slice direction, respectively. In such an ultrasound sensor 1, it is possible to continuously acquire, in the scanning direction, sensing information in the slice direction by performing driving, that is, performing transmission and reception of ultrasonic waves for each row extending in the slice direction while scanning in the scanning direction.

In Embodiment 1 of the invention, it is possible to significantly improve the transmission sensitivity and the reception sensitivity at the same time by providing the ultrasound element 10 optimized to the dedicated reception type and the ultrasound element 10 optimized to the dedicated transmission type together in the slice direction in a state where they share the uniform resonance frequency.

Figure 9:
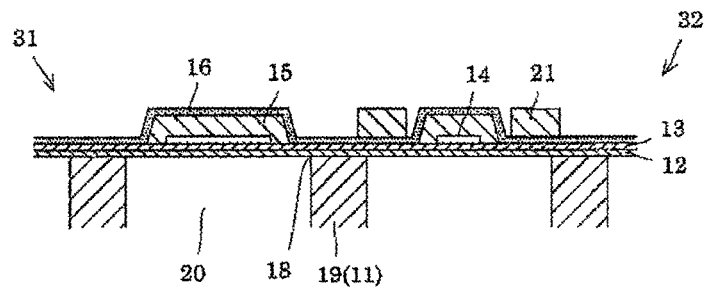
FIG. 9 shows an exemplary ultrasound element optimized to the dedicated transmission type or the dedicated reception type.
Figure 10:
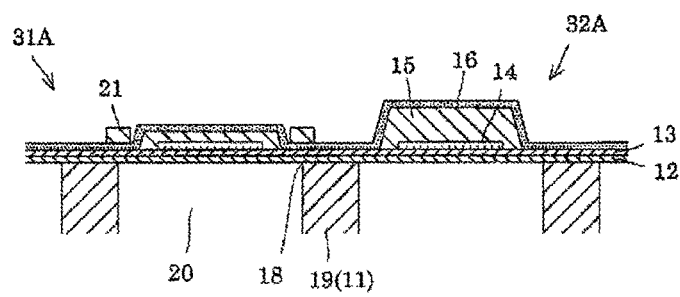
FIG. 10 shows an exemplary ultrasound element optimized to the dedicated transmission type or the dedicated reception type.
Figure 11:
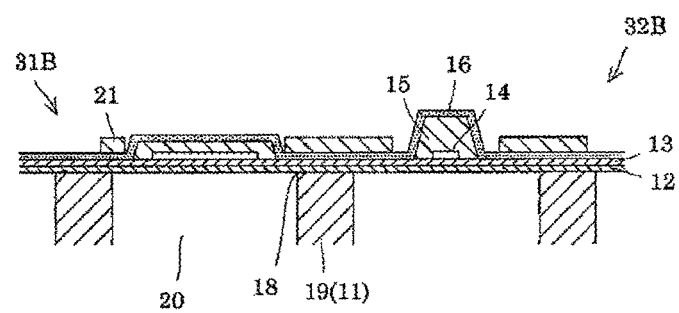
FIG. 11 shows an exemplary ultrasound element optimized to the dedicated transmission type or the dedicated reception type.

FIGS. 9 to 11 show examples of the ultrasound element optimized to the dedicated transmission type and the ultrasound element 10 optimized to the dedicated reception type.

FIG. 9 shows the ultrasound elements which are optimized to the dedicated transmission type and the dedicated reception type by varying the width of the active portion. A dedicated transmission element 31, which is the ultrasound element 10 optimized to the dedicated transmission type, has a relatively large width of the active portion. A dedicated reception element 32, which is the ultrasound element 10 optimized to the dedicated reception type, has a relatively small width of the active portion. The resonance frequency adjustment film 21 is provided on the lateral side of the active portion apart therefrom.

With such a configuration, it is possible to realize the dedicated transmission element 31 optimized to the dedicated transmission type and the dedicated reception element 32 optimized to the dedicated reception type, and also possible to adjust them to have the same resonance frequency by providing the resonance frequency adjustment film 21.

Example A shown in the following table 1 represents a specific example in a case where an aspect ratio of the short side and the long side is assumed to be 1:4 or more. The configuration of Example 1A has the resonance frequency of 1.7 MHz, while the resonance frequency of Example 2A varies to 1.5 MHz by varying the width of the piezoelectric body/the width of the opening portion. As shown in Example 3A, the resonance frequency becomes 1.7 MHz by providing the resonance frequency adjustment film (formed of, for example, titanium-tungsten) with Young's modulus of 300 Gpa and a thickness of 270 nm. That is, it is possible to allow the configuration of 3A to have the same resonance frequency as that of the configuration of 1A. Moreover, the resonance frequency can be also adjusted to 1.7 MHz by varying the width of the opening portion of 2A, as shown in Example 4A.

The invention is not limited to a case where the aspect ratio is 1:4 or more.

TABLE 1

| Example A | Example 1A | Example 2A | Example 3A | Example 4A |
|---|---|---|---|---|
| Width of piezoelectric body/width of opening portion | 0.7 | 0.3 | 0.3 | 0.3 |
| Width of opening portion [μm] | 70 | 70 | 70 | 66 |
| Width of second electrode [μm] | 49 | 49 | 49 | 19.8 |
| Width of first electrode [μm] | 37 | 37 | 37 | 15 |
| Young's modulus [Gpa] | | | 300 | |
| Thickness [nm] | | | 270 | |
| Resonance Frequency [MHz] | 1.7 | 1.5 | 1.7 | 1.7 |

FIG. 10 shows the ultrasound elements which are optimized to the dedicated transmission type and the dedicated reception type by varying the thickness of the active portion. A dedicated transmission element 31A, which is the ultrasound element 10 optimized to the dedicated transmission type, has a relatively small thickness of the active portion. A dedicated reception element 32A, which is the ultrasound element 10 optimized to the dedicated reception type, has a relatively large thickness of the active portion. The resonance frequency adjustment film 21 is provided on the lateral side of the active portion of the dedicated transmission element 31A, apart therefrom.

Example B shown in the following table 2 represents a specific example in a case where an aspect ratio of the short side and the long side is assumed to be 1:4 or more. As shown in Example 2B, the resonance frequency varies by varying the thickness of the piezoelectric body with respect to the configuration of Example 1B. As shown in Example 3B, the resonance frequency becomes 1.7 MHz by providing the resonance frequency adjustment film (formed of, for example, titanium-tungsten) with Young's modulus of 300 Gpa and a thickness of 250 nm. That is, it is possible to allow the configuration of 3B to have the same resonance frequency as that of the configuration of 1B. Moreover, the resonance frequency can be also adjusted to 1.7 MHz by varying the width of the opening portion of 2B, as shown in Example 4B. The invention is not limited to a case where the aspect ratio is 1:4 or more.

TABLE 2

| Example B | Example 1B | Example 2B | Example 3B | Example 4B |
|---|---|---|---|---|
| Thickness of piezoelectric body [μm] | 1250 | 700 | 700 | 700 |
| Width of piezoelectric body/width of opening portion | 0.7 | 0.3 | 0.3 | 0.3 |
| Width of opening portion [μm] | 70 | 70 | 70 | 66 |
| Width of second electrode [μm] | 49 | 49 | 49 | 19.8 |
| Width of first electrode [μm] | 37 | 37 | 37 | 15 |
| Young's modulus [Gpa] | | | 300 | |
| Thickness [nm] | | | 250 | |
| Resonance Frequency [MHz] | 1.7 | 1.5 | 1.7 | 1.7 |

With such a configuration, it is possible to realize the dedicated transmission element 31A optimized to the dedicated transmission type and the dedicated reception element 32A optimized to the dedicated reception type, and also possible to adjust them to have the same resonance frequency by providing the resonance frequency adjustment film 21.

FIG. 11 shows the ultrasound elements which are optimized to the dedicated transmission type and the dedicated reception type by varying the thickness and the width of the active portion. A dedicated transmission element 31B, which is the ultrasound element 10 optimized to the dedicated transmission type, has a relatively large width and a relatively small thickness of the active portion. A dedicated reception element 32B, which is the ultrasound element 10 optimized to the dedicated reception type, has a relatively small width and a relatively large thickness of the active portion. The resonance frequency adjustment films 21 are provided on the lateral sides of the active portions of both the dedicated transmission element 31B and the dedicated reception element 32B, apart therefrom.

With such a configuration, it is possible to realize the dedicated transmission element 31B optimized to the dedicated transmission type and the dedicated reception element 32B optimized to the dedicated reception type, and also possible to adjust them to have the same resonance frequency by providing the resonance frequency adjustment film 21.

In the examples shown in FIGS. 9 to 11, the dedicated transmission element and the dedicated reception element may be adjusted such that the reception resonance frequency is equal to the integral multiple of the transmission resonance frequency, instead of sharing the same resonance frequency. Such an ultrasound sensor can be used in non-linear imaging.

The non-linear imaging is a method for separating and imaging high-frequency components which are generated by distortion occurred in the intravitally-emitting ultrasound pulse and are not contained in the transmission wave.

In the examples shown FIGS. 9 to 11, the width of the opening portion is not varied. However, the transmission-reception sensitivity may be varied and optimized by varying the width of the opening portion together with, or instead of varying the width of the active portion.

In the examples shown FIGS. 9 to 11, the resonance frequency adjustment film 21 is exemplified as the resonance frequency adjustment portion. However, the resonance frequency adjustment portion is not limited thereto. A bonding portion protruded toward a side of the substrate 11 may be provided on a bonding substrate bonded to the substrate 11 such that the bonding portion presses against a region in which the resonance frequency adjustment film 21 is provided, or the resonance frequency adjustment film 21 itself.

The bonding substrate is, for example, a protective substrate for sealing and protecting the ultrasound element 10, which has a space for covering whole ultrasound elements 10. However, the bonding substrate is not limited thereto.

As stated above, in Embodiment 1, the dedicated transmission element and the dedicated reception element, each of which is optimized to the transmission sensitivity and the reception sensitivity, respectively, are provided together by varying the width or thickness of the active portion, while the dedicated transmission element and the dedicated reception element share the uniform resonance frequency by providing the resonance frequency adjustment film. With such a configuration, the transmission characteristic and the reception characteristic can be improved at the same time. The transmission and reception can be effectively performed since the dedicated transmission element and the dedicated reception element share the same resonance frequency.

Other Embodiments

Although not described in each of the above-described embodiments, it is possible to use a configuration in which the opposite side to the piezoelectric element 17 of the diaphragm becomes a pass-through region for ultrasonic waves transmitted towards a measurement target or ultrasound waves reflected from the measurement target (echo signal). Accordingly, it is possible to simplify the configuration of the opposite side to the piezoelectric element of the diaphragm, and possible to ensure a favorable pass-through region for ultrasonic waves and the like. An electrical region of the electrodes, wirings and the like and the contact and fixing region of each member is distanced from the measurement target, and it becomes easier to prevent contamination or leakage current between these and the measurement target. Accordingly, it is possible to also favorably apply the invention a medical device which is particularly averse to contamination or leakage current, for example, ultrasound diagnostic equipment, blood pressure gages, and eye pressure gages.

In general, the opening portion 18 of the substrate 11 is filled with a resin serving as the acoustic matching layer, such as silicone oil, a silicone resin or a silicone rubber, and the opening portion 18 is sealed with a lens member through which the ultrasound can be passed. Thereby, the acoustic impedance difference between the piezoelectric element 17 and the measurement target can be reduced, and the ultrasound can be transmitted efficiently to the measurement target side.

Furthermore, although not described in the above-described embodiments, it is preferable that a sealing plate that seals the region which includes the piezoelectric element 17 is bonded to the substrate 11. Thereby, because it is possible to physically protect the piezoelectric element 17, and the strength of the ultrasound sensor 1 also increases, it is possible to increase the structural stability. It is possible for the handling properties of the ultrasound sensor 1 which includes the piezoelectric elements 17 to be improved in a case where the piezoelectric elements 17 are formed as thin films.

In the above-described embodiment, although an example is given in which the opening portion 18 is formed for each piezoelectric element 17, there is no limitation thereto, and the openings may be formed corresponding to a plurality of piezoelectric elements 17. For example, an opening which is shared by a row of piezoelectric elements 17 arranged along the scanning direction may be provided or one opening may be formed for all piezoelectric elements 17. Although the vibration states of the piezoelectric elements 17 become different in a case where an opening shared for a plurality of piezoelectric elements 17 is provided, a pressing member or the like is provided between each of the piezoelectric elements 17 from the opposite side to the substrate 11 of the diaphragm, and similar vibration may be performed as a case where independent openings are provided.

Figure 12:
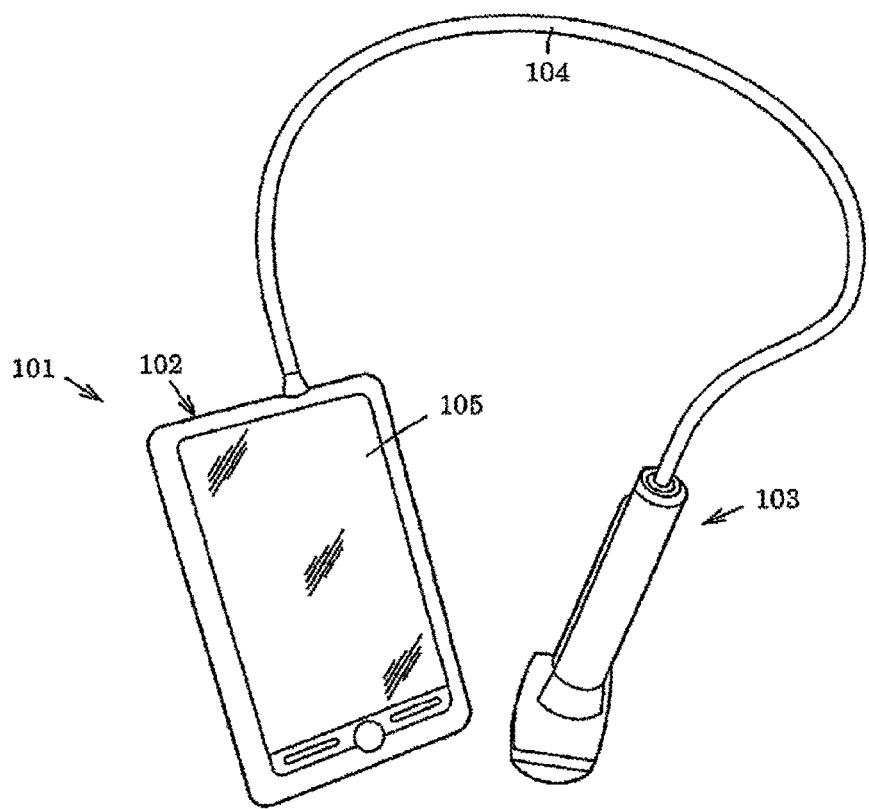
FIG. 12 is a perspective view illustrating an example of an ultrasonic diagnostic apparatus.
Figure 13:
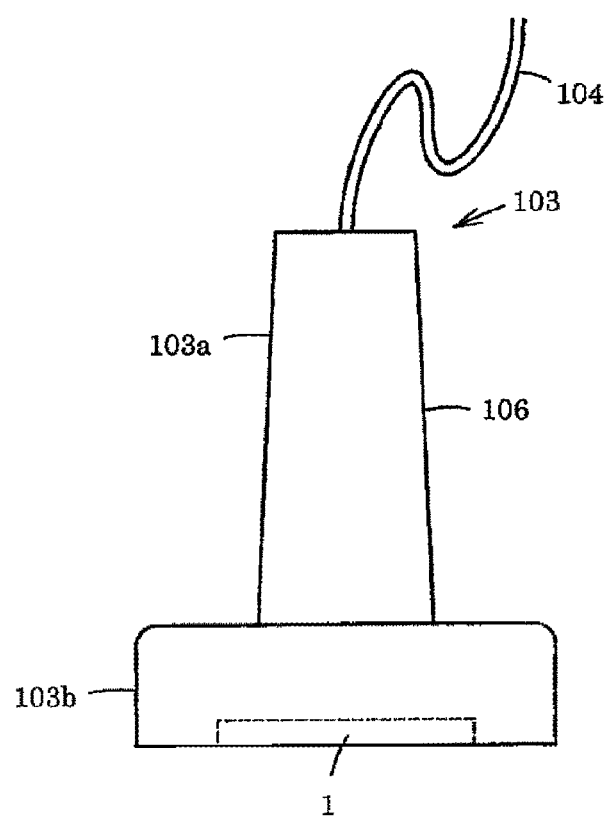
FIG. 13 is a side view illustrating an example of an ultrasound probe.

Here, an example of an ultrasonic diagnostic apparatus using the ultrasound sensor described above will be described. FIG. 12 is a perspective view illustrating a schematic configuration of an example of the ultrasonic diagnostic apparatus, and FIG. 13 is a cross-sectional view illustrating the ultrasound probe.

As illustrated in the drawings, an ultrasonic diagnostic apparatus 101 is provided with a device terminal 102 and an ultrasound probe (probe) 103. The device terminal 102 and the ultrasound probe 103 are connected by a cable 104. The device terminal 102 and the ultrasound probe 103 exchange electrical signals through the cable 104. A display panel (display device) 105 is incorporated in the device terminal 102. A screen of the display panel 105 is exposed in the surface of the device terminal 102. In the device terminal 102, an image is generated based on ultrasonic waves transmitted from the ultrasound sensor 1 of the ultrasound probe 103 and detected. The imaged detection results are displayed on the screen of the display panel 105.

The ultrasound probe 103 includes a housing 106. The ultrasound sensor 1 in which a plurality of ultrasound sensor elements 10 are two-dimensionally arranged in the first direction X and the second direction Y is stored in the housing 106. The ultrasound sensor 1 is provided so that the surface thereof is exposed in the surface of the housing 106. The ultrasound sensor 1 outputs ultrasonic waves from the surface and receives the reflected waves of the ultrasound. It is possible to provide the ultrasound probe 103 with a probe head 103b which is freely detachable from the probe main body 103a. At this time, it is possible for the ultrasound sensor 1 to be incorporated in the housing 106 of the probe head 103b. The ultrasound sensor 1 is formed with the ultrasound sensor elements 10 arranged two-dimensionally in the first direction X and the second direction Y.

The invention claimed is:

1. An ultrasound sensor, comprising:
a substrate on which an opening portion is formed;
a diaphragm which is provided on the substrate so as to block the opening portion; and
ultrasound elements which include a first electrode, a piezoelectric layer and a second electrode and which are laminated on an opposite side to the opening portion of the diaphragm, wherein
when a direction in which the first electrode, the piezoelectric layer and the second electrode are laminated is referred to as a Z-direction, a portion in which the first electrode, the piezoelectric layer and the second electrode are overlapped in the Z-direction is referred to as an active portion, and a portion which is a range to the extent that the diaphragm is oscillatable by driving the active portion is referred to as a movable portion,
the active portion is arranged opposite to the movable portion;
the active portion has a smaller profile than that of the movable portion in a plan view; and
a resonance frequency adjustment portion for adjusting a resonance frequency is provided on a lateral side of the active portion, at least in a region opposite to the movable portion such that a majority of the resonance frequency adjustment portion is located outside of the movable portion in the plan view,
wherein the resonance frequency adjustment portion includes a length that extends in a y-direction and a width that extends in an x-direction, the width overlaps an edge of the opening portion that extends in the y-direction, and the length of the resonance frequency adjustment portion is less than a length of the edge of the opening portion that extends in the y-direction.

2. The ultrasound sensor according to claim 1,
wherein, in plan view, the active portion is in a rectangle shape, and
the resonance frequency adjustment portion is provided on a lateral side of a long side of the rectangle shape.

3. The ultrasound sensor according to claim 1,
wherein a plurality of the movable portions and the active portions are arranged in at least one of the X-direction and Y-direction.

4. The ultrasound sensor according to claim 3,
wherein the resonance frequency adjustment portions are provided on lateral sides of a portion of the plurality of the active portions, while the resonance frequency adjustment portions are not provided on lateral sides of other portion of the plurality of the active portions.

5. The ultrasound sensor according to claim 3, wherein two or more types of the active portions are provided, each of which has the piezoelectric layer having a different width such that the width is a length of any one of the sides in the X-direction or the Y-direction in a case where the active portion is in a square shape and the width is a length of a short side in a case where the active portion is in a rectangle shape, in plan view.

6. The ultrasound sensor according to claim 3, wherein two or more types of the active portions are provided, each of which has the piezoelectric layer having a different thickness.

7. The ultrasound sensor according to claim 3, wherein the plurality of ultrasound elements include the ultrasound element set as a dedicated reception type and the ultrasound element set as a dedicated transmission type.

8. The ultrasound sensor according to claim 1, wherein the resonance frequency adjustment portion is composed of a material different from those of the first electrode, the piezoelectric layer and the second electrode.

9. The ultrasound sensor according to claim 1, wherein the second electrode extends continuously along a surface of the diaphragm facing away from the substrate.

10. The ultrasound sensor according to claim 9, wherein the resonance frequency adjustment portion is positioned on an exposed surface of the second electrode.

11. The ultrasound sensor according to claim 9, wherein the piezoelectric layer comprises manganese (Mn).

* * * * *